United States Patent
Williams et al.

(10) Patent No.: US 12,131,620 B2
(45) Date of Patent: Oct. 29, 2024

(54) PERSONAL SAFETY SYSTEM

(71) Applicant: Robert Bosch GmbH, Stuttgart (DE)

(72) Inventors: Aimee Williams, Troy, MI (US); Christopher Prediger, Novi, MI (US); Danielle Heinz, Hemlock, MI (US); Steffen Kutter, Bietigheim-Bissingen (DE); Jia Hou, Kornwestheim (DE); Sylvia Briese, Benningen am Neckar (DE); Camille Vuillaume, Tokyo (JP)

(73) Assignee: Robert Bosch GmbH, Stuttgart (DE)

( * ) Notice: Subject to any disclaimer, the term of this patent is extended or adjusted under 35 U.S.C. 154(b) by 210 days.

(21) Appl. No.: 17/455,732

(22) Filed: Nov. 19, 2021

(65) Prior Publication Data
US 2023/0162590 A1  May 25, 2023

(51) Int. Cl.
*H04W 4/90* (2018.01)
*A61B 5/024* (2006.01)
*A61B 5/0245* (2006.01)
*G06V 20/58* (2022.01)
*G06V 40/10* (2022.01)
(Continued)

(52) U.S. Cl.
CPC ........ *G08B 25/016* (2013.01); *A61B 5/02438* (2013.01); *A61B 5/02455* (2013.01); *G06V 20/58* (2022.01); *G06V 40/10* (2022.01); *G06V 40/20* (2022.01); *G08B 21/02* (2013.01); *G08B 25/10* (2013.01); *H04W 4/023* (2013.01); *H04W 4/027* (2013.01); *H04W 4/12* (2013.01); *H04W 4/90* (2018.02); *H04W 4/40* (2018.02); *H04W 4/80* (2018.02)

(58) Field of Classification Search
CPC ........................... G08B 25/016; H04W 12/086
USPC ......................................................... 455/411
See application file for complete search history.

(56) References Cited

U.S. PATENT DOCUMENTS 8,552,855 B2 * 10/2013 Herickhoff ......... G06Q 10/1095
340/539.11
9,378,532 B2   6/2016 Herickhoff et al.
(Continued)

FOREIGN PATENT DOCUMENTS

GB        2464507        4/2010

OTHER PUBLICATIONS

Tep Wireless, Kitestring personal safety service, available at: https://www.kitestring.io/faq, available at least as early as Jul. 22, 2021 (4 pages).
(Continued)

*Primary Examiner* — Qutbuddin Ghulamali
(74) *Attorney, Agent, or Firm* — Maginot, Moore & Beck LLP (57) ABSTRACT

A method of operating a personal safety system including a vehicle includes automatically detecting that a smartphone is within a communication range using a wireless communication system of the vehicle, and starting an approach time period with a controller of the vehicle or the smartphone when the smartphone is detected. The method further includes sending checkup data from the vehicle to the smartphone using the wireless communication system when the smartphone fails to arrive at the vehicle prior to the approach time period elapsing, and triggering an emergency response by the vehicle and/or the smartphone when the vehicle fails to receive a response to the checkup data from the smartphone within a response time period.

20 Claims, 4 Drawing Sheets

(51) Int. Cl.
*G06V 40/20* (2022.01)
*G08B 21/02* (2006.01)
*G08B 25/01* (2006.01)
*G08B 25/10* (2006.01)
*H04W 4/02* (2018.01)
*H04W 4/12* (2009.01)
*H04W 4/40* (2018.01)
*H04W 4/80* (2018.01)

(56) References Cited

U.S. PATENT DOCUMENTS

| | | | |
|---|---|---|---|
| 10,286,875 B2 * | 5/2019 | Penilla | B60L 50/66 |
| 10,419,907 B2 * | 9/2019 | Redding | H04W 4/80 |
| 10,432,774 B2 * | 10/2019 | Simon | G08B 25/016 |
| 10,807,567 B2 * | 10/2020 | Salter | B60R 25/31 |
| 11,057,511 B2 | 7/2021 | Graham | |
| 2007/0153993 A1 * | 7/2007 | Cohen | H04M 11/002 |
| | | | 379/38 |
| 2014/0306799 A1 * | 10/2014 | Ricci | G06V 40/166 |
| | | | 340/5.83 |
| 2019/0168712 A1 * | 6/2019 | Yakovenko | B60R 25/24 |
| 2020/0135005 A1 * | 4/2020 | Katz | H04M 7/0021 |
| 2021/0001807 A1 * | 1/2021 | Park | H04W 12/04 |
| 2021/0337460 A1 * | 10/2021 | Breaux, III | H04W 8/18 |

OTHER PUBLICATIONS

Emergensee, personal security app, available at least as early as Jul. 22, 2021 (2 pages).

* cited by examiner

PERSONAL SAFETY SYSTEM

FIELD

This disclosure relates to the field of safety systems and/or security systems and, in particular, to personal safety systems and/or personal security systems.

BACKGROUND

The market includes numerous personal safety applications ("apps") and wearable safety devices such as watches, necklaces, and panic buttons. These apps and devices provide a sense of security when the user is in a dangerous place or a place perceived to be dangerous. For example, users, including both women and men, frequently use personal safety apps and safety devices when walking alone through parking lots and parking garages to increase the feeling of security in these dangerous places.

Known personal safety apps and devices typically provide users with an increased feeling of security; however, these apps and devices may be ineffective when the user encounters a sudden and unexpected confrontation, emergency, and/or otherwise stressful situation. For example, some personal safety apps and devices require the user to provide tactile inputs to a smartphone during the unexpected confrontation. If the user "freezes up" during the confrontation, then the user may be unable to operate the smartphone and, therefore, unable to activate the safety features of the app.

Based on the above, personal safety apps and safety devices can be improved to provide safety services to users even when the users are unable to access the personal safety app and/or the safety device.

SUMMARY

According to an exemplary embodiment of the disclosure, a method of operating a personal safety system with a vehicle includes automatically detecting that a smartphone is within a communication range using a vehicle's wireless communication system and starting an approach time period with a controller of the vehicle or the smartphone when the smartphone is detected. The method further includes sending checkup data from the vehicle to the smartphone using the wireless communication system when the smartphone fails to arrive at the vehicle prior to the approach time period elapsing, and triggering an emergency response by the vehicle and/or the smartphone when the vehicle fails to receive a response to the checkup data from the smartphone within a response time period.

According to another exemplary embodiment of the disclosure, a personal safety system includes a wireless communication system of a vehicle and a controller. The wireless communication system is configured to automatically detect that a smartphone is within a communication range of the wireless communication system. The controller is operably connected to the wireless communication system. The controller is configured to start an approach time period when the smartphone is detected by the wireless communication system, and to send checkup data from the vehicle to the smartphone using the wireless communication system when the smartphone fails to arrive at the vehicle prior to the approach time period elapsing. The controller is further configured to trigger an emergency response by the vehicle and/or the smartphone when the vehicle fails to receive a response to the checkup data from the smartphone within a response time period.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Aspects of the disclosure are disclosed in the accompanying description. Alternate embodiments of the disclosure and their equivalents may be devised without parting from the spirit or scope of the disclosure. It should be noted that any discussion herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

For the purposes of the disclosure, the phrase "A and/or B" means (A), (B), or (A and B). For the purposes of the disclosure, the phrase "A, B, and/or C" means (A), (B), (C), (A and B), (A and C), (B and C), or (A, B and C).

The terms "comprising," "including," "having," and the like, as used with respect to embodiments of the disclosure, are synonymous.

Figure 1:
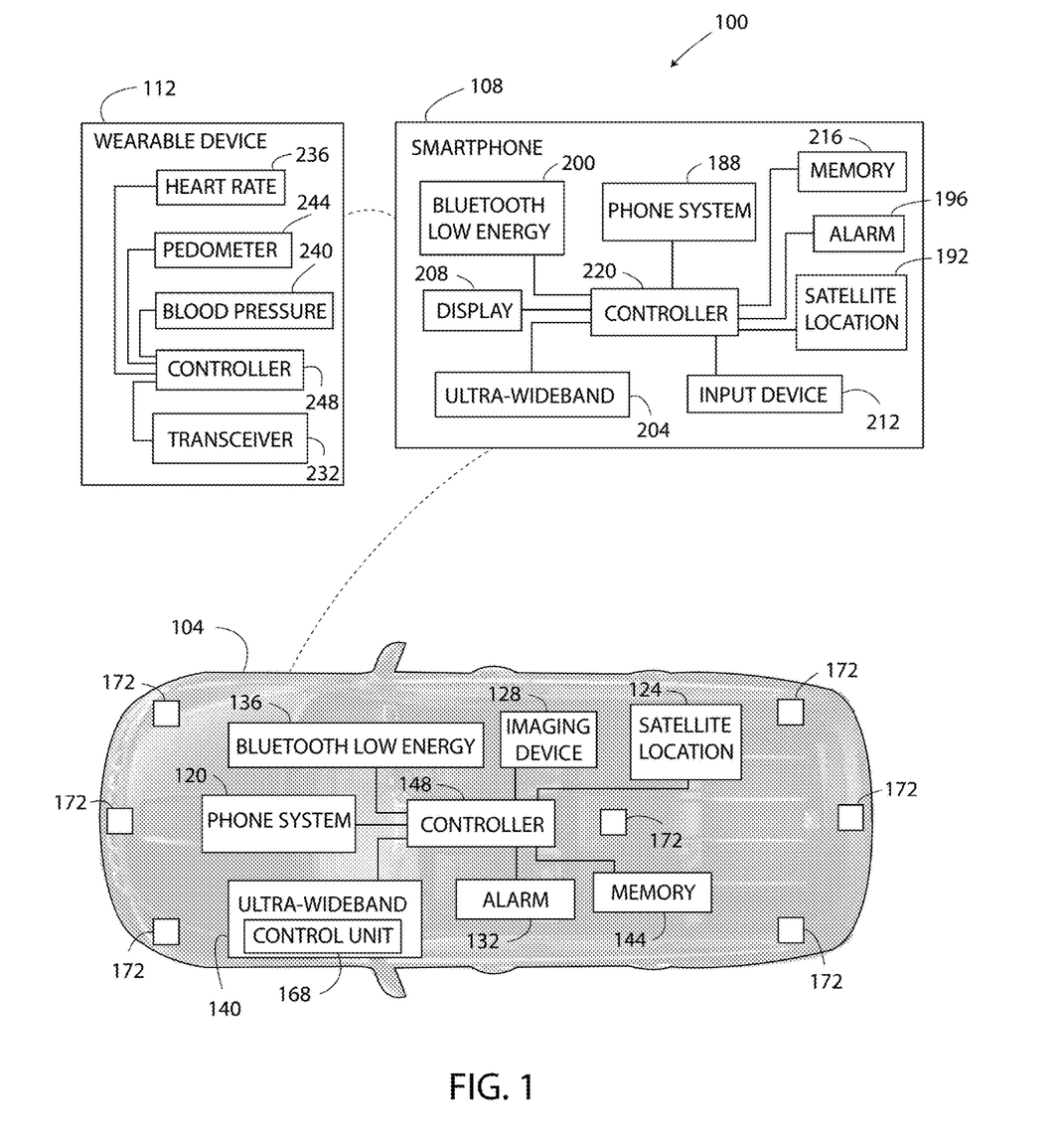
FIG. 1 is a block diagram of a personal safety system for use with a vehicle, a smartphone, and, optionally, a wearable device.

As shown in FIG. 1, a personal safety system 100 is configured for use with a vehicle 104, a smartphone 108, and, optionally, a wearable device 112. The personal safety system 100 is configured to provide an automatic emergency response when the personal safety system 100 detects that the user associated with the smartphone 108 is in an unsafe condition. To initiate the emergency response, the personal safety system 100 requires no inputs or actions from the user and, therefore, is fully automatic. As such, even when the user "freezes" due to extreme stress or otherwise becomes incapacitated, the personal safety system 100 is operable to automatically trigger the emergency response. Each element of the personal safety system 100 and a method 300 (FIG. 3) of operation are described herein.

The vehicle 104 includes a phone system 120, a satellite location system 124, an imaging device 128, an alarm system 132, a Bluetooth Low Energy system 136, an ultra-wideband system 140, and a memory 144 each operably connected to a controller 148. The vehicle 104 is a passenger car, light truck, or sport utility vehicle. In other embodiments, the vehicle 104 is any road-going vehicle including commercial vehicles, such as semi-trailer trucks. Moreover, the vehicle 104 includes operator-controlled vehicles, partially-automated vehicles, fully-automated vehicles, and autonomous vehicles. The vehicle 104 also includes shared vehicles, rented vehicles, and personal vehicles. Accordingly, the safety benefits of the personal safety system 100 are provided to users of all types vehicles 104.

As shown in FIG. 1, the phone system 120 of the vehicle 104, in one embodiment, is a cellular phone system configured to place and to receive voice calls using an associated cellular network (not shown). The phone system 120 is an exemplary wireless communication system. The phone system 120 is a wireless and mobile phone system that is further configured to receive text messages, to send text messages, to receive voicemail messages, and/or to send voicemail messages. In one embodiment, the phone system 120 is operably connected to the Internet through the cellular network and is further configured to send and to receive email messages. The phone system 120 is configured for user control, such as by a user of the vehicle 104. The phone system 120 is also configured for automatic operation in which a voice call, a text message, a smartphone notification, a voicemail, and/or an email is automatically generated and sent. In some embodiments, the phone system 120 operates as a voice over internet protocol (VoIP) system in addition to or in alternative to utilizing the cellular network. The phone system 120 is operably connected to an infotainment system, display screen, a speaker system, and/or a microphone of the vehicle 104.

With continued reference to FIG. 1, the satellite location system 124 of the vehicle 104 is configured to generate location data that is representative of the location of the vehicle 104 on the Earth. In one embodiment, the satellite location system 124 includes a Global Positioning System (GPS) receiver configured to receive GPS signals from GPS satellites (not shown). The location system 124 is configured to process the received GPS signals and to generate the location data therefrom. The location data, in one embodiment, includes latitude and longitude information. Additionally or alternatively, the location data includes a street address, a nearby crossroad, and/or a nearby landmark such as a business name or other well-known feature. The location system 124, in some embodiments, is further configured to generate altitude data. Additionally or alternatively, the location system 124 includes or is configured to operate with any other satellite navigation system including, but not limited to, the European Union's Galileo system and China's BeiDou navigation satellite system. In some embodiments, the vehicle 104 does not include the satellite location system 124, and the personal safety system 100 uses a satellite location system 192 (FIG. 1) of the smartphone 108.

Figure 2:
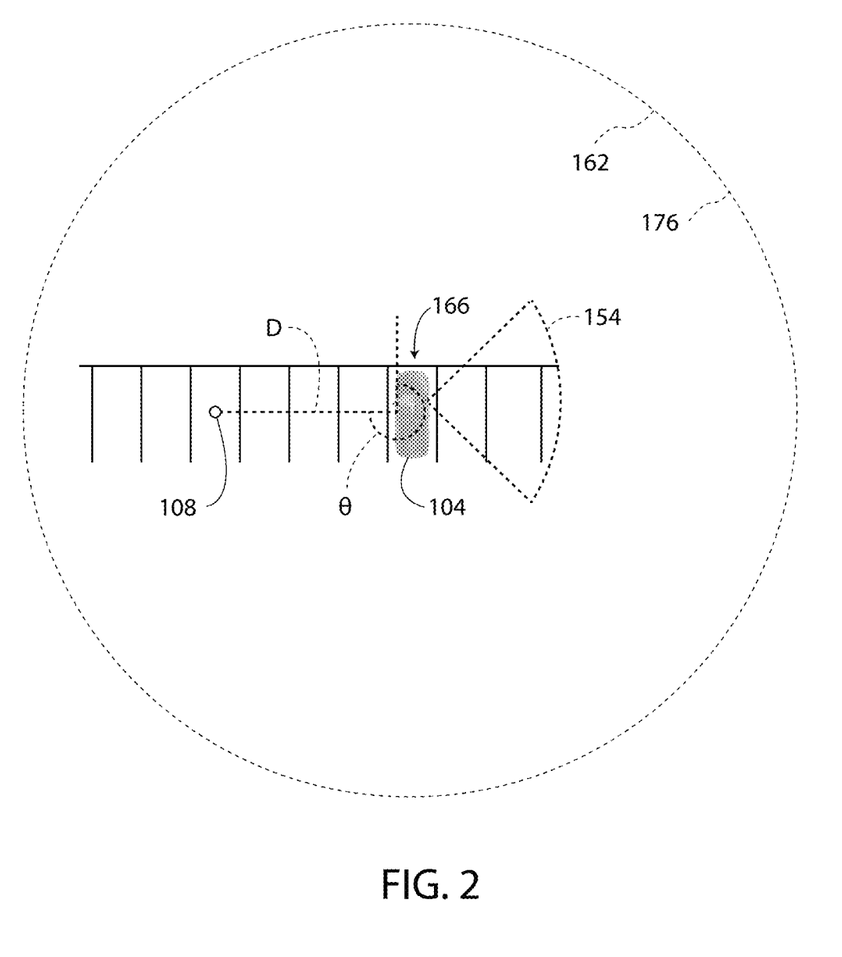
FIG. 2 is block diagram of the personal safety system of FIG. 1, shown as a top view of the vehicle and the smartphone in a parking garage.

The imaging device 128 is positioned on the vehicle 104 and is configured to generate digital image data representative of an exterior area (i.e. outside a cabin of the vehicle 104). As shown in FIG. 2, the imaging device 128 defines a field of view 154 and is configured to generate the image data within the field of view 154. The imaging device 128 or devices are mounted on the vehicle 104, such that the image data is generated from the driver side, from the passenger side (as shown in FIG. 2), from the front side, and/or from the back side of the vehicle 104. Accordingly, the vehicle 104 may include a plurality of the imaging devices 128. The imaging device 128 is configured as a thermal camera, an infrared camera, and/or a visible light camera. The vehicle 104 may include any one or more of the above-described types of imaging devices 128. Additionally or alternatively, the imaging device 128 generates the image data of the cabin of vehicle 104, such that the personal safety system 100 is further configured to determine if a potentially unauthorized person is in the vehicle 104. In other embodiments, the vehicle 104 does not include the imaging device 128 and does not generate the image data.

With reference again to FIG. 1, the alarm system 132 of the vehicle 104 is configured to generate sound and/or light to draw the attention of other people to the vehicle 104. The alarm system 132, in one embodiment, activates a horn of the vehicle 104 to generate attention getting sounds. Additionally or alternatively, the alarm system 132 includes a siren or other noise making device that is activated to generate the attention getting sounds. Moreover, the alarm system 132 may be configured to flash the headlights, taillights, brake lights, and/or parking lights of the vehicle 104 to generate light, which tends to attract the attention of other people to the vehicle 104.

The Bluetooth low energy (BLE) system 136 is another exemplary wireless communication system for electronic communication between the vehicle 104 and the smartphone 108. Specifically, the BLE system 136 is a wireless personal area network configured to wirelessly send data to the smartphone 108 and to wirelessly receive data from the smartphone 108 within a communication range 162 (FIG. 2) of the BLE system 136. That is, the BLE system 136 and the smartphone 108 are configured for communication with each other. The communication range 162 is not shown to scale in FIG. 2 and may be larger or smaller than shown as compared to the size of the vehicle 104. The BLE system 136 is configured to periodically broadcast messages (referred to as advertising packets and/or message data) in an attempt to establish a wireless data connection with a nearby paired device, such as the smartphone 108. The distance from the vehicle 104 that the broadcasted messages are receivable is the communication range 162 of the BLE system 136. The communication range 162 is substantially circular as viewed from above. In a typical BLE system 136, the communication range 162 is approximately one hundred meters (100 m) from the vehicle 104 in all directions. The smartphone 108, for example, is configured to automatically form the wireless data connection with the BLE system 136 when the smartphone is 100 m or less from the vehicle 104 in response to receiving one or more of the advertising packets. In FIG. 2, the smartphone 108 is within the communication range 162 and is connected to the BLE system 136. In other embodiments, the communication range 162 of the BLE system 136 is from five meters (5 m) to one hundred fifty meters (150 m).

In one embodiment, when the vehicle 104 is parked and in a non-driving mode (and typically unoccupied) as shown in FIG. 2, the BLE system 136 remains powered and periodically broadcasts the advertising packets according to an advertising interval. An exemplary advertising interval is selected from the range of 20 ms to ten seconds (10 s). In one embodiment, a preferred advertising interval is 500 ms. Thus, when the vehicle 104 is parked in a parking space 166, or any other place, and is unoccupied, the BLE system 136 periodically broadcasts the advertising packets in an attempt to establish the wireless data connection to the smartphone 108 (or other suitable paired device) as soon as the smartphone 108 is in the communication range 162. In some embodiments, the BLE system 136 periodically broadcasts the advertising packets when the vehicle 104 is parked and is locked. The vehicle 104 may be occupied or unoccupied during broadcasting of the advertising packets.

A shown in FIG. 1, the ultra-wideband system 140 is another exemplary wireless communication system for electronic communication between the vehicle 104 and the smartphone 108. In one embodiment, the ultra-wideband system 140 includes a control unit 168 and a plurality of anchor units 172 operably connected to the control unit 168. The anchor units 172, also referred to herein as a plurality of modules of a second wireless communication system, are fixedly connected to the vehicle 104 and are each configured to communicate with a paired device, such as the smartphone 108. In one embodiment, a controller area network (CAN) bus connects the anchor units 172 to the control unit 168. In other embodiments, any other desired electrical connection system is used to connect the anchor units 172 to the control unit 168. The ultra-wideband system 140 defines a communication range 176 (FIG. 2) that is approximately the same size as the communication range 162 of the BLE system 136. For example, the communication range 176 of the ultra-wideband system 140 is approximately one hundred meters (100 m). The communication range 176 is substantially circular, as viewed from above, and is the distance from the vehicle 104 that the ultra-wideband system 140 is configured to transmit data to the smartphone 108 (or other connected and paired device) and to receive data from the smartphone 108. In other embodiments, the communication range 176 of the ultra-wideband system 140 is from twenty-five meters (25 m) to two hundred meters (200 m).

The ultra-wideband system 140 is configured to use time of flight (ToF) signal measurements between the anchor units 172 and the smartphone 108 to generate position data of the smartphone 108 for monitoring a position of the smartphone 108. The position data identifies the precise location of the smartphone 108 relative to the vehicle 104. For example, as shown in FIG. 2, in one embodiment, the position data includes a distance D and an angle θ. The distance D corresponds to the straight-line distance of the smartphone 108 from a reference point of the vehicle 104, such as the driver's side door. The angle θ of the position data identifies from which direction the smartphone 108 is approaching the vehicle 104. In one embodiment, the front of the vehicle 104 (according to a forward driving direction) is identified as zero degrees (0° and an opposite rear of the vehicle 104 is identified as one hundred eighty degrees (180°). Accordingly, for a left-hand drive vehicle 104, if the position data is 20 m at two hundred seventy degrees)(270° (as shown in FIG. 2), then the connected smartphone 108 is 20 m from the driver's side door on the driver's side of the vehicle 104. In other embodiments, any other coordinate system is used to identify the position of the smartphone 108 relative to the vehicle 104, such as a rectangular coordinate system.

As shown in FIG. 1, the memory 144 of the vehicle 104 is an electronic storage device that is configured to store at least the location data, the image data, the position data, and program instruction data for operating the personal safety system 100. The memory 144 is also configured to store contact data for use by the phone system 120. Specifically, the memory 144 stores data corresponding to a predetermined emergency contact phone number. The user of the personal safety system 100 is able to configure the specific phone number or numbers stored in the memory 144 as the predetermined emergency contact phone number or numbers. The memory 144 may store a plurality of predetermined emergency contact phone numbers that are called by the phone system 120 in a prioritized order as set by the user of the personal safety system 100. The predetermined emergency contact phone numbers may include the phone numbers of a family member, a friend, the police department, 911, the fire department, a hospital, a colleague, a university safety department, a parking garage attendant, a building security team, and/or any other phone number as desired by the user. The memory 144 is also referred to herein as a non-transitory computer readable medium.

The controller 148 of the vehicle 104 is configured to execute the program instruction data in order to operate the personal safety system 100. The controller 148 is provided as at least one microcontroller and/or microprocessor. In one embodiment, the CAN bus of the vehicle 104 operably connects the controller 148 to the phone system 120, the satellite location system 124, the imaging device 128, the alarm system 132, the Bluetooth Low Energy system 136, the ultra-wideband system 140, and the memory 144.

The controller 148 is configured to generate checkup data that is transmitted to the smartphone 108 using the BLE system 136, for example. As explained in detail herein, the checkup data is sent to the smartphone 108 when the personal safety system 100 determines that the user of the smartphone 108 may be experiencing an emergency.

With reference again to FIG. 1, the smartphone 108 of the personal safety system 100 includes a phone system 188, a satellite location system 192, an alarm system 196, a BLE system 200, an ultra-wideband system 204, a display 208, an input device 212, and a memory 216 each operably connected to a controller 220. The phone system 188, in one embodiment, is a cellular phone system configured to place and to receive voice calls using the cellular network. The phone system 188 is an exemplary wireless communication system. The phone system 188 is a wireless and mobile phone system that is further configured to receive text messages, to send text messages, to receive voicemail messages, to send voicemail messages, to receive email messages, and to send email messages. In one embodiment, the phone system 188 is operably connected to the Internet through the cellular network. The phone system 188 is configured for user control, such as by a user of the smartphone 108. The phone system 188 is also configured for automatic operation in which a voice call, a text message, a smartphone notification, a voicemail, and/or an email is automatically generated and sent to another device. In some embodiments, the phone system 188 operates as a voice over internet protocol (VoIP) system in addition to or in alternative to utilizing the cellular network. The phone system 188 is operably connected to the display screen 208, a speaker system, and a microphone of the smartphone 108.

The satellite location system 192 of the smartphone 108 is configured to generate location data that is representative of the location of the smartphone 108 on the Earth. In one embodiment, the satellite location system 192 is or includes a Global Positioning System (GPS) receiver configured to receive GPS signals from a GPS satellite (not shown).

Additionally or alternatively, the satellite location system 192 includes or is configured to operate with any other satellite navigation system including, but not limited to, the European Union's Galileo system and China's BeiDou navigation satellite system. The location data, in one embodiment, includes latitude and longitude information. The satellite location system 192, in some embodiments, is further configured to generate altitude data.

As shown in FIG. 1, the alarm system 196 of the smartphone 108 is configured generate sound and/or light to draw attention to the smartphone 108 and the user of the smartphone 108. The alarm system 196, in one embodiment, activates the speaker of the smartphone 108 to generate attention getting sounds and activates the display 208 of the smartphone 108 to generate attention getting light.

The BLE system 200 of the smartphone 108, which is another exemplary wireless communication system, is configured to operate with the BLE system 136 of the vehicle 104. In one embodiment, the smartphone 108 is a client device and the vehicle 104 is a central device to which the client device establishes the wireless data connection. In another embodiment, the BLE system 200 of the smartphone 108 is the central device and the BLE system 136 of the vehicle 104 is the client device. The BLE system 200 of the smartphone 108, when connected to the BLE system 136 of vehicle 104, enables wireless electronic data transmission between the smartphone 108 and the vehicle 104. In response to receiving one or more of the broadcasted periodic messages from the BLE system 136, the BLE system 200 is configured to generate connection data for establishing the wireless data connection with the BLE system 136. The connection data includes any data used to establish the wireless data connection between the BLE systems 136, 200. The connection data are transmitted between the smartphone 108 and the BLE system 136 of the vehicle 104. The BLE system 136 of the vehicle 104 is configured for communication with the BLE system 200 of the smartphone 108.

The ultra-wideband system 204 of the smartphone 108, which is another exemplary wireless communication system, is configured to operate with the ultra-wideband system 140 of the vehicle 104. In particular, the ultra-wideband system 204 communicates with the anchor units 172 to enable the control unit 168 to determine the position data of the smartphone 108. The ultra-wideband system 204 of the smartphone 108, when connected to the ultra-wideband system 140 of vehicle 104, enables wireless electronic data transmission between the smartphone 108 and the vehicle 104, and enables the vehicle 104 to determine the position data.

The display 208 of the smartphone 108, in one embodiment, is a liquid crystal display (LCD) panel configured to render and to display text, images, and other user sensible outputs and visually comprehensible data. For example, the display 208 is configured to render data, such as a graphical user interface (GUI) for controlling the smartphone 108. The display 208 is also configured to render the checkup data generated by the vehicle 104. In a specific embodiment, the display 208 is configured to render a GUI associated with an app of the personal safety system 100. Using the app, the user views and may respond to the checkup data, for example.

The input device 212 of the smartphone 108 is a touchscreen applied over the display 208 that is configured to respond to the touch of a finger or a stylus by generating user input data. In another embodiment, the input device 212 includes at least one button that is configured to generate input data when touched or moved by a user. In yet another embodiment, the input device 212 is any device configured to generate an input signal and/or input data, as desired by those of ordinary skill in the art.

The memory 216 of the smartphone 108 is a non-transitory computer readable storage medium that is configured to store data for operating a smartphone 108. The memory 216 is configured to store app data, the input data, the location data of the location system 192 and any other data for operating or controlling the smartphone 108, such as response data generated in response to the checkup data.

The controller 220 of the smartphone 108 includes at least one microprocessor and/or microcontroller and is configured to generate data, as described herein, for controlling the smartphone 108. The controller 220 is configured to run applications (i.e. "apps") stored as app data including the app of the personal safety system 100. The personal safety system 100 may include an app run on the controller 220 of the smartphone 108.

As shown in FIG. 1, the wearable device 112 includes a transceiver 232 and at least one heartrate sensor 236, a blood pressure sensor 240, and a pedometer 244 operably connected to a controller 248. As noted above, the wearable device 112, is an optional element of the personal safety system 100; accordingly, certain embodiments of the personal safety system 100 do not include the wearable device 112. The wearable device 112 is typically a wearable health monitor, watch, necklace, or health tracking device that is operably connected to the smartphone 108. For example, in one embodiment the wearable device 112 is worn around the wrist of the user of the smartphone 108. In some embodiments, the wearable device 112 is further operably connected to the vehicle 104.

The transceiver 232 of the wearable device 112 is operably connected to a corresponding transceiver of the smartphone, such as one of the BLE system 200 and the ultra-wide band system 204. The transceiver 232 is configured for the wireless exchange of electronic data with the smartphone 108 and/or the vehicle 104. For example, the transceiver 232 wirelessly transmits vital sign data from the wearable device 112 to the smartphone 108. In other embodiments, the transceiver 232 exchanges data with the smartphone 108 using Wi-Fi, Bluetooth®, near-field communication (NFC), and/or any other wireless network protocol.

The heartrate sensor 236 is configured to generate vital sign data corresponding to the heartrate, heartbeat, and/or pulse of the wearer of the wearable device 112. For example, the heartrate sensor 236 may detect the wearer's heartrate as seventy beats per minute (70 bpm) and generate corresponding vital sign data. In an exemplary embodiment, the heartrate sensor 236 is an optical heartrate sensor configured to detect the wearer's heartrate at the wearer's wrist. In other embodiments, the heartrate sensor 236 is provided as any other wearable heartrate sensor.

The blood pressure sensor 240 is configured to generate vital sign data corresponding to the blood pressure of the wearer of the wearable device 112. For example, the blood pressure sensor 240 may detect the wearer's blood pressure as 120/80 mmHg and generate corresponding vital sign data. In an exemplary embodiment, the blood pressure sensor 240 is an indirect blood pressure monitoring device that operates by measuring and detecting pulse transit time. In other embodiments, the blood pressure sensor 240 is provided as any other wearable blood pressure sensor.

The pedometer 244 is configured to generate vital sign data corresponding to motion of the wearer of the wearable device and, in particular, to the number of footsteps taken by the wearer and the speed of the wearer relative to the vehicle 104. For example, the pedometer 244 may detect that the wearer is moving at a walking pace (i.e. five kilometers per hour (5 kph)) and is taking one hundred steps per minute. In an exemplary embodiment, the pedometer 244 is a piezo-electric-type pedometer. In other embodiments, the pedometer 244 is provided as any other wearable pedometer.

The controller 248 of the wearable device 112 includes at least one microprocessor and/or microcontroller and is configured to generate data, as described herein, for controlling the wearable device 112.

Figure 3:
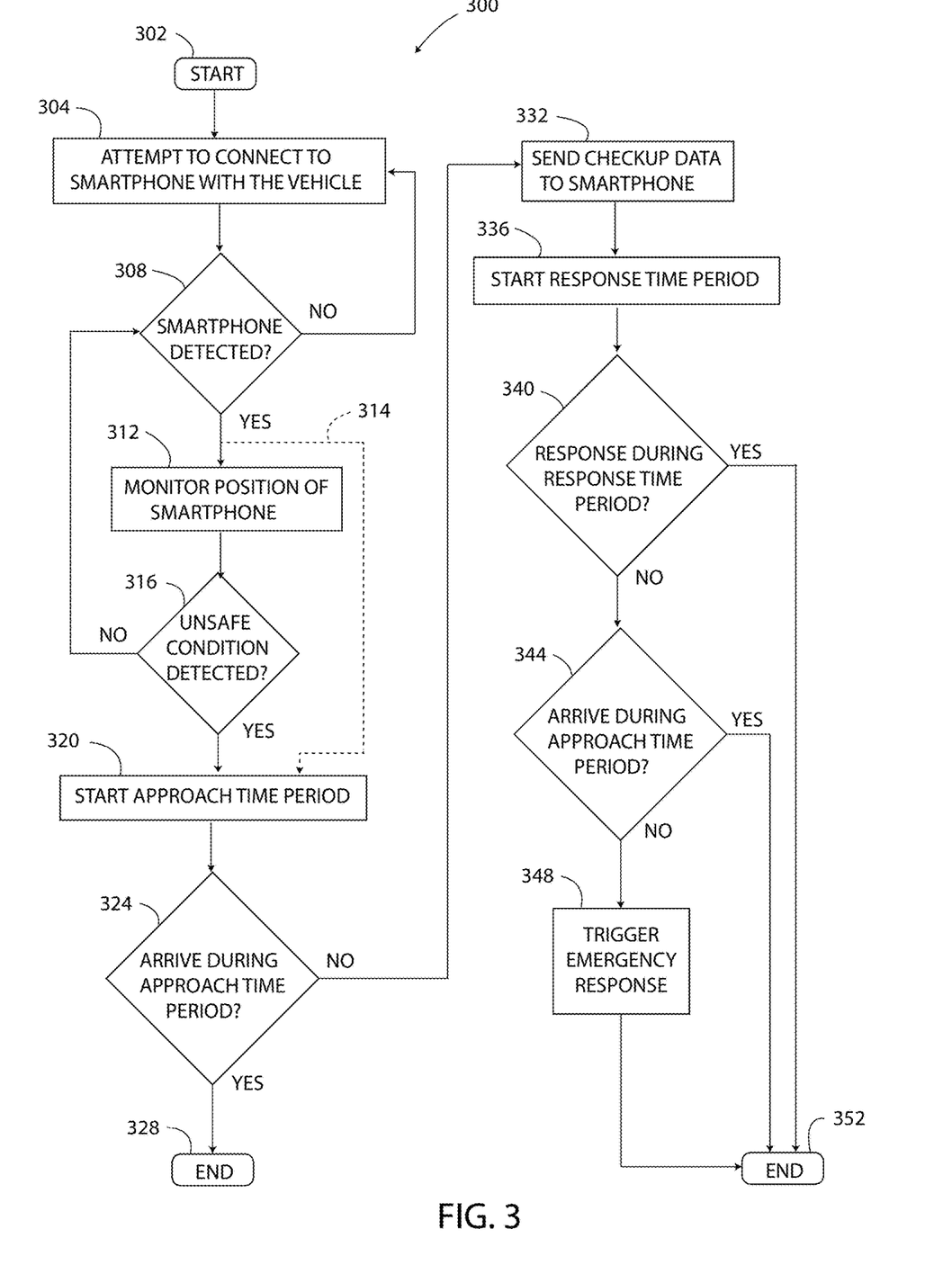
FIG. 3 is a flowchart illustrating an exemplary method of operating the personal safety system of FIG. 1.

In operation and with reference to FIG. 3, the flowchart illustrates an exemplary method 300 for operating the personal safety system 100. The personal safety system 100, in one embodiment, includes an app on the smartphone 108 and/or the vehicle 104. The app of the personal safety system 100 is automatically run when booting the smartphone 108 so that the personal safety system 100 is available and ready when needed. The app of the personal safety system 100, in one embodiment, is run continuously on the vehicle 104. Additionally or alternatively, the app of the personal safety system 100 is manually stopped and started by the user of the smartphone 108. The app of the personal safety system 100 implements the method 300 of FIG. 3, which starts at block 302.

As shown at blocks 304 and 308, the method 300 includes attempting to establish a wireless data connection with the smartphone 108 using the vehicle 104 to enable the vehicle 104 to automatically detect the presence of the smartphone 108 within the communication range 162 of the BLE system 136. Accordingly, the personal safety system 100, integrated directly into the vehicle 104, in one embodiment. To this end, the controller 148 causes the BLE system 136 of the vehicle 104 to periodically broadcast the messages (i.e. the advertising packets). In one embodiment, the advertising packets are periodically broadcast from the vehicle 104 whenever the vehicle 104 is parked so that the smartphone 108 is automatically detected anytime the smartphone 108 enters the commination range 162 of the BLE system 136. The app of the personal safety system 100 on the smartphone 108 instructs the smartphone 108 to wirelessly connect to the vehicle 104 when the broadcasted messages are received.

At block 308, when the wireless data connection between the vehicle 104 and the smartphone 108 is not established, then the smartphone 108 is not detected and the vehicle 104 continues to broadcast the messages. Whereas, when the wireless data connection between the smartphone 108 and the vehicle 104 is established, then the smartphone 108 is within the communication range 162 of the BLE system 136 and the smartphone 108 is automatically detected by the vehicle 104. The smartphone 108 is detected by sending and receiving electronic data between the BLE systems 136, 200, for example. In one embodiment, the BLE system 136 of the vehicle 104 detects that the smartphone 108 is within the communication range 162 when the BLE system 136 of the vehicle 104 receives the connection data sent from the BLE system 200 of the smartphone 108. The smartphone 108 generates the connection data in response to receiving one of the broadcasted periodic messages. The connection data are transmitted from the BLE system 200 of the smartphone 108 to the BLE system 136 of the vehicle 104 over the wireless data connection.

Next, at blocks 312 and 316 of FIG. 3, the method 300 includes monitoring the position of the smartphone 108 using the vehicle 104 and determining if an unsafe condition is present. As described herein, some embodiments of the personal safety system 100 do not monitor the position of the smartphone 108 (block 312) and do not detect the unsafe condition (block 316). Instead, as shown by the branch 314, in some embodiments, when the smartphone 108 is detected by the vehicle 104, the method 300 proceeds directly to block 328. Accordingly, blocks 312 and 316 of the method 300 are optional.

At block 312 of the method 300, the personal safety system 100 monitors the position of the smartphone 108 within the communication range 176 of the ultra-wideband system 140 and generates the position data that correspond to the position of the smartphone 108. In particular, the control unit 168 of the ultra-wideband system 140 processes the ToF signals from the anchor units 172 to determine the specific position of the smartphone 108 relative to the vehicle 104. The position data, in one embodiment, are stored in the memory 144 of the vehicle 104.

Figure 4:
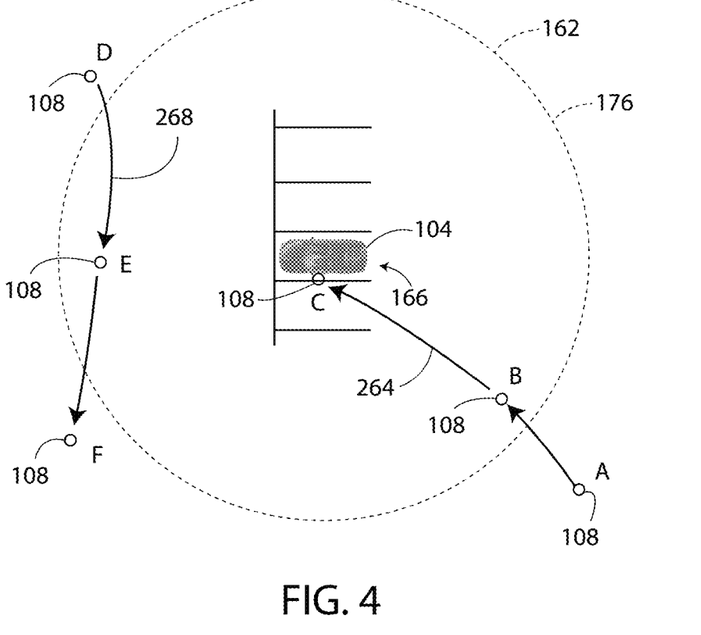
FIG. 4 is a block diagram of the personal safety system of FIG. 1, shown as a top view of the vehicle and the smartphone in a parking garage, two paths of the smartphone are identified each of which results in the detection of a safe condition by the personal safety system.

At block 316 of the method 300, the personal safety system 100 detects if user of the smartphone 108 is experiencing an unsafe condition or a safe condition using the controller 148, 220 of the vehicle 104 or the smartphone 108. The safe condition is detected as any condition that is not an "unsafe condition" and includes processing the position data to detect that the smartphone 108 is approaching the vehicle 104 without any delays and in a typical, normal, or expected manner. Two exemplary safe conditions are shown in FIG. 4 as path 264 and path 268. In FIG. 4, the vehicle 104 is parked in a parking space 166, there are no occupants in the vehicle 104, and the vehicle 104 is in a locked configuration. At position A of the path 264, the smartphone 108 is outside of the communication range 162 and is not detected by the BLE system 136 of the vehicle 104. At positions B and C of the path 264, the smartphone 108 is within the communication range 162 and is detected by the BLE system 136 and the ultra-wideband system 140 of the vehicle 104 to generate the position data. At position C, the user opens the driver's side door of the vehicle 104 and enters the vehicle 104, in this example. Since the path 264 taken by the smartphone (and the corresponding user) to the vehicle 108 proceeds without delay, in a smooth course, and in an expected manner, the safe condition is detected in connection with the path 264.

When the safe condition is detected at block 316 (i.e. no unsafe condition is detected), the method 300 loops back to block 308 to determine if the wireless data connection between the vehicle 104 and the smartphone 108 still exists. The path 268 of FIG. 4 shows that the smartphone 108 may enter and exit the communication range 162 of the BLE system 136 without triggering an emergency response from the personal safety system 100. For example, at position D the smartphone 108 is outside of the communication range 162 and is not detected by the BLE system 136. At position E, the smartphone 108 is within the communicant range 162 and is detected by the BLE system 136. The position data at position E do not trigger an unsafe condition. At position F, the smartphone 108 is not detected by the BLE system 136 and has left the communication range 162. Since, the safe condition was detected at position E, no emergency action is taken by the personal safety system 100. The user on the path 268, for example, walked by the parked vehicle 104 without needing or wanting to access or approach the vehicle 104, as may occur for any number of reasons.

At block 316, the unsafe condition is detected according to at least three approaches. A first approach for detecting the unsafe condition includes detecting that the smartphone 108 is within the communication range 162 of the BLE system 136, but that the position of the smartphone 108 is stationary or substantially stationary. As used herein, the smartphone 108 is "substantially stationary" when the position data indicate that the smartphone 108 is staying within two meters (2 m) of a detected position.

Figure 5:
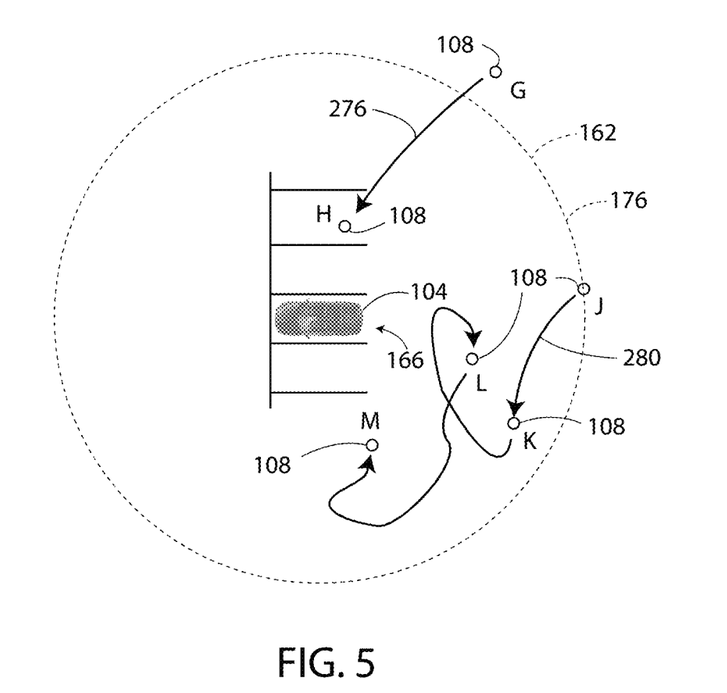
FIG. 5 is a block diagram of the personal safety system of FIG. 1, shown as a top view of the vehicle and the smartphone in a parking garage, two paths of the smartphone are identified each of which results in the detection of an unsafe condition by the personal safety system.

For example, with reference to FIG. 5, the smartphone 108 moves on a path 276 toward the vehicle 104. The smartphone 108 is not detected at position G, and the smartphone is detected by the BLE system 136 at position H. At position H, however, the smartphone 108 stops moving toward the vehicle 104, is stationary, or is substantially stationary. When the controller 148 determines that the smartphone 108 is stationary or substantially stationary, a predetermined time period is started by the controller 148 of the vehicle 104 or the controller 220 of the smartphone 108. If the smartphone 108 is stationary or substantially stationary for the duration of the predetermined time period, then the unsafe condition is detected. As an example, a user is approaching the vehicle 104 along the path 276 carrying shopping bags or other goods. It is expected that the user approaches the vehicle 104 without delay. At position H, however, another person has drawn the attention of the user and (i) wants to engage in friendly conversation with the user, (ii) wants to harm the user, (iii) wants to take the user's goods, or (iv) has otherwise distracted the user. One or more of these events causes the user to become stationary or substantially stationary at position H relative to the vehicle 104, which is a deviation from the expected behavior of the user. Based on the above, the detected unsafe condition could be a friendly encounter, or the detected unsafe condition could be the beginning of a dangerous situation.

At block 316, a second approach for detecting the unsafe condition includes detecting that the user's path to the vehicle 104 is erratic. Most users when approaching the vehicle 104 take a generally straight path to the driver's side door, the passenger side door, or to the trunk of the vehicle 104. As shown in FIG. 5, however, the position data, as detected by the ultra-wideband system 140, indicates that the user has taken an erratic path 280 to the vehicle 104 that includes moving to positions J, K, L, and M. The erratic path 280 is detected by the indirect, looping, and/or zig-zag movements of the smartphone 108 as determined from the position data of the ultra-wideband system 140. When an erratic path 280 is identified, the unsafe condition is detected at block 316 of the method 300. The erratic path 280 may be innocuous, however, the erratic path 280 is a deviation from the expected behavior and is identified as an unsafe condition by the controller 148 or the controller 220.

At block 316, a third approach for detecting the unsafe condition includes monitoring the vital sign data generated by the optional wearable device 112 that is operably connected to the smartphone 108. Typically, when a user approaches the vehicle 104, the user's vital signs are within a normal or expected range. However, during an unexpected confrontation, emergency, and/or otherwise stressful situation, the user's heartrate and blood pressure tend to be elevated above normal levels and/or outside of the normal or expected range. Accordingly, in one embodiment, the unsafe condition is detected by the controller 148, 220 at block 316 when the user's heartrate is compared to a predetermined heartrate and the user's heartrate exceeds the predetermined heartrate. The predetermined heartrate is set by the user and/or is automatically determined by the personal safety system 100 based on the user's age and/or average heartrate data. In another embodiment, the unsafe condition is detected by the controller 148, 220 at block 316 when the user's heartrate is outside of a predetermined heartrate range. Specifically, the unsafe condition is detected when the user's heartrate is above an upper limit of the predetermined heartrate range and when the user's heartrate is below a lower limit of the predetermined heartrate range. An exemplary predetermined heartrate range is from forty beats per minute (40 bpm) to one hundred forty beats per minute (140 bpm). The predetermined heartrate range is set by the user and/or is automatically determined by the personal safety system 100 based on the user's age and/or average heartrate data. In another embodiment, the unsafe condition is detected by the controller 148, 220 at block 316 when the user's blood pressure is compared to a predetermined blood pressure and the user's blood pressure exceeds the predetermined blood pressure. The predetermined blood pressure is set by the user and/or is automatically determined by the personal safety system 100 based on the user's age and/or average blood pressure data. In a further embodiment, the unsafe condition is detected by the controller 148, 220 at block 316 when the user's blood pressure is outside of a predetermined blood pressure range. Specifically, the unsafe condition is detected when the user's blood pressure is above an upper limit of the predetermined blood pressure range and when the user's blood pressure is below a lower limit of the predetermined blood pressure range. An exemplary predetermined blood pressure range is based on systolic blood pressure and is from 70 mmHg to 140 mmHg. The predetermined blood pressure range is set by the user and/or is automatically determined by the personal safety system 100 based on the user's age and/or average blood pressure data.

For example, with reference to the path 276 of FIG. 5, when the user's heartrate exceeds the predetermined heartrate any time that the smartphone 108 is detected by the vehicle 104, then the unsafe condition is detected. That is, on the path 276 when the heartrate data exceeds the predetermined heartrate, then the unsafe condition is detected prior to the smartphone 108 arriving at position H and prior to the determination of the stationary or substantially stationary positioning.

In some embodiments at block 316, the vital sign data and the position data are processed conditionally to detect the safe condition or the unsafe condition. For example, when the smartphone 108 is detected as being stationary or substantially stationary, then the controller 148, 220 processes the vital sign data to monitor the user's heartrate and/or blood pressure. If the controller 148, 220 determines that the heartrate and/or blood pressure are below the predetermine value(s) and/or within the predetermined range(s), then a safe condition is detected even though the smartphone 108 is stationary or substantially stationary. This is because the user has remained calm during the stationary or substantially stationary period and is likely taking a break or having a friendly conversation. If the user were engaged in an unexpected confrontation, emergency, and/or otherwise stressful situation, then the vital sign data would instead tend to indicate that the heartrate and/or the blood pressure exceed the predetermined value(s) and/or are outside of the predetermined range(s). For example, in a stressful situation a typical user will exhibit an elevated heartrate and blood pressure that exceed the upper limits of the corresponding predetermined ranges. As an additional example, if the user is experiencing significant medical trauma, then the user may exhibit a reduced heartrate and blood pressure that are below the lower limits of the corresponding predetermined ranges. Vital signs above and below the limits of the predetermined ranges are used to detect the unsafe condition.

At block 316, the unsafe condition may also be detected based on the data generated by the pedometer 244 of the optional wearable deice 112. A user typically approaches the vehicle 104 below a predetermined speed. If the personal safety system 100 determines that the user is moving within the communication range 176 above the predetermined speed, then the unsafe condition is detected at block 316. The predetermined speed is set by the user and/or is automatically determined by the personal safety system 100 based on the user's age and/or average speed. For example, if the user is being chased by an attacker and/or is running away from a dangerous situation, then the user's speed tends to exceed the predetermined speed. As another example, if the user is simply finishing a running exercise then the user's speed may exceed the predetermined speed and the user's vital sign data tend to exceed the predetermined values. Thus, the unsafe condition detected based on the data from the pedometer 244 may correspond to an actual unsafe condition or an innocuous event that has caused the user to move faster than expected.

Next, at block 320 of FIG. 3, the personal safety system 100 starts an approach time period. As noted above, blocks 312 and 316 are optional. Thus, personal safety system 100 may arrive at block 320 from block 316 after detection of the unsafe condition, or the personal safety system 100 may arrive at block 320 immediately after detecting the smartphone 108 according to branch 314 of the flowchart of FIG. 3. The approach time period may be calculated and/or monitored by either the controller 148 of the vehicle 104 and/or the controller 220 of the smartphone 108.

When the position detection of blocks 312 and 316 are included in the method 300, the duration of the approach time period is calculated based on (i) the distance of the smartphone 108 from the vehicle 104 when the unsafe condition is detected, and (ii) the normal walking speed of the user. For example, if the unsafe condition is detected when the smartphone 108 is seventy-five meters (75 m) from the vehicle 104, then with a typical walking pace of 5.0 kph, the approach time period is set to fifty-four seconds (54 s).

When the position detection block 312 and 316 are not included in the method 300, the duration of the approach time period is based on the size of the communication range 162 and the time required for the user to walk to the vehicle 104 at a normal walking pace. For example, if the communication range 162, under most conditions, extends one hundred meters (100 m) from the vehicle 104, then with a typical walking pace of 5.0 kph, the approach time period is set to seventy-two seconds (72 s).

At block 328, when personal safety system 100 determines that the smartphone 108 (and the user) has arrived at the vehicle 104 prior to the approach time period elapsing, then the method 300 ends and no emergency response is triggered by the personal safety system 100. The personal safety system 100 determines that the smartphone 108 has arrived at the vehicle 104 according to any suitable approach including (i) detecting that a door of the vehicle 104 has been opened, (ii) detecting that a rear hatch or trunk of the vehicle 104 has been opened, (iii) detecting that the user has touched an electronically touch-sensitive portion of the vehicle 104, such as a door handle that causes the vehicle 104 doors to unlock, and/or (iv) detecting that a key fob of the vehicle 104 and/or the smartphone 108 is located inside of the cabin of the vehicle 104 using the ultra-wideband system 140 or any other detection system. When none of the above-listed events occur, then the personal safety system 100 determines that the smartphone 108 has failed to arrive at the vehicle 104 at block 324.

No emergency response is triggered when the controller 148, 220 determines that the smartphone 108 has arrived at the vehicle 104 prior to elapsing of the approach time period, because that is the expected action of the user and even if an emergency situation is occurring, then the user can take appropriate actions once located in the cabin of the vehicle 104 with the doors locked, if needed. For example, in connection with the path 280 of FIG. 5, if the smartphone 108 arrives to the vehicle 104 prior to elapsing of the approach time period, then the detected unsafe condition of the erratic path 280 was merely an unusual motion taken by the user and is no cause for concern. Similarly, in connection with the path 276 of FIG. 5, if the smartphone 108 arrives to the vehicle 104 prior to elapsing of the approach time period, then the stationary position of the smartphone 108 was innocuous and is no cause for concern. If the unsafe condition is detected based on the user vital signs, but the smartphone 108 arrives to the vehicle 104 prior to elapsing of the approach time period, then the user may have been exercising or is more excited than usual and there is no cause for concern. In embodiments without the position detection of blocks 312 and 316, if the smartphone 108 arrives to the vehicle 104 prior to elapsing of the approach time period, then the user has safely arrived in the cabin of the vehicle 104 and there is no cause for concern.

At block 332 of the method 300 shown in FIG. 3, the smartphone 108 is located within the communication range 162 of the BLE system 136 and has failed to arrive at the vehicle 104 prior to elapsing of the approach time period. Accordingly, the user has been delayed and is taking longer to arrive at the vehicle 104 than expected by the personal safety system 100. Reasons for the delay may be innocuous or may be an indication that the user is in a dangerous situation and/or is experiencing a medical emergency.

At block 332 the controller 148, 220 causes the phone system 120 of the vehicle 104 to send the checkup data to the smartphone 108. The checkup data is a text, phone call, notification, and/or any other mechanism for causing the smartphone 108 to gain the attention of the user. The checkup data requests a response from the user. For example, the checkup data is a text message sent to the smartphone 108 that results in the smartphone 108 making an audible noise, a vibration, and/or causing the display 208 to illuminate. The text of the text message requests the user to confirm that they are safe and/or not in need of medical assistance. In other embodiments, the checkup data is a phone call from the phone system 120 of the vehicle 104 to the phone system 188 of the smartphone 108. Upon receiving the phone call, the smartphone 108 makes an audible noise, vibrates, and/or illuminates the display 208. In embodiments including the wearable device 112, the checkup data may be displayed on a display of the wearable device 112 (if so equipped) and/or the wearable device 112 may emit an audible noise in response to the smartphone 108 receiving the checkup data.

Next at block 336, the method 300 includes starting a response time period for the user to respond to the checkup data that is sent to the smartphone 108. In one embodiment, the response time period is thirty seconds (30 s). In other embodiments, the response time period is from 10 seconds (10 s) to sixty seconds (60 s) or any other suitable time period. The duration of the response time period, in one embodiment, is configurable by the user. The controller 148 of the vehicle 104 and/or the controller 220 of the smartphone 108 may be configured to start and to count the duration of the response time period.

At block 340 the method 300 includes determining if the user has responded to the checkup data during the response time period. The personal safety system 100 monitors for a user response during the response time period to attempt to avoid an unnecessary triggering of an emergency response and to provide the user with an opportunity to confirm their safety. The user responds to the checkup data in any suitable manner including, sending a response text message from the smartphone 108 to the vehicle 104, acknowledging the notification generated by the smartphone 108, and/or answering the phone call from the vehicle 104.

At block 352, when the user responds to the checkup data during the response time period then the method 300 ends, because the user has confirmed their safety. For example, on the path 276 of FIG. 5, the smartphone 108 was detected as being stationary or substantially stationary at position H. Accordingly, at block 320 the approach time period is started and at block 324 it is determined that smartphone 108 and the user have not arrived to the vehicle 104. At block 332, the vehicle 104 sends the checkup data, which in this example is a text message, and at block 336 the response time period is started by either the controller 220 of the smartphone 108 or the controller 148 of the vehicle 104. In this example, the user is merely talking to an acquaintance at position H and the user responds to the text message with a follow-up text message of any information or data to indicate that she is safe. Accordingly, the method 300 ends at block 352 even though the user has not arrived to the vehicle 104 because the user's safety has been confirmed by the personal safety system 100.

At block 344 the personal safety system 100 has detected that the user has not responded to the checkup data, and the personal safety system 100 has also detected that the user has arrived at the vehicle 104 within the approach time period. Accordingly, even though the user did not respond to the checkup data, the user's safety is confirmed because the user and the smartphone 108 are located in the cabin of the vehicle 104. Accordingly, the method 300 ends at block 352.

If, however, at block 344 the user did not respond to the checkup data and the smartphone 108 and user did not arrive at the vehicle 104 during the approach time period, then the method 300 advances to block 348 in which the personal safety system 100 triggers an emergency response. In order to arrive at block 348 and trigger the emergency response, the user has not responded to the checkup data and has not arrived at the vehicle 104. Accordingly, the personal safety system 100 has determined that the user is in peril and requires assistance. The peril may be the result of an attacker or a medical emergency experienced by the user.

The specific type of emergency response triggered by the personal safety system 100 at block 348 may be configurable by the user. An exemplary emergency response includes activating the alarm 132 of the vehicle 104 and/or activating the alarm 196 of the smartphone 108. The emergency response may also include activing either the phone system 120 or the phone system 188 to automatically call or text an emergency services department, such as the police department (e.g. 911), the fire department, and/or a local hospital. Additionally or alternatively, the emergency response includes automatically calling the predetermined emergency contact phone number with either of the phone systems 120, 188. Additionally or alternatively, the emergency response includes sending an email message to a predetermined email contact or to the email address of a medical provider or an emergency services provider. No action by the user is needed in order for the personal safety system 100 to trigger the emergency response. The emergency response is performed by the smartphone 108 and/or the vehicle 104.

When the personal safety system 100 performs the emergency response, the personal safety system 100 may transmit the location data to the device and/or the person receiving the emergency response. For example, the automated call to the police department or the predetermined emergency contact phone number may automatically provide the device or person receiving the call with the name of the user and the location of the user based on the location data. The automated call also indicates that the user is in need of police, fire, and/or medical assistance and that a response should be sent immediately. The automated call is in the language most typically spoken in the country in which the user is located.

As an example, the smartphone 108 is stationary or substantially stationary at position H in FIG. 5 because, in this example, the user has encountered a sudden and unexpected confrontation, emergency, and/or otherwise stressful situation. The user has not arrived at the vehicle 104 and has not responded to the checkup data. The user may have been attacked, may have "frozen" in fear, may have had a medical emergency (e.g., heart attack or stroke), and/or is otherwise incapacitated. Accordingly, at block 348 the personal safety system 100 initiates the emergency response and a call to 911 is automatically placed by the phone system 188 of the smartphone 108 or the phone system 120 of the vehicle 104. The automatic call provides the emergency dispatcher with the name of the user, a request for assistance, and the location data (e.g., a street address or other location identifier). The user has taken no action and the emergency services have been automatically alerted. That is, the call to "911" has been made without any user inputs to the vehicle 104 or the smartphone 108, and without requiring the user to access the smartphone 108 during the emergency. Thus, the personal safety system 100 has automatically assisted the user and emergency services have been alerted of the user's troubles without delay.

Additionally or alternatively, the personal safety system 100 is configured to provide alerts to the user in advance of a potentially dangerous situation. For example, the personal safety system 100 is configured to process the image data generated by the imaging device 128 to detect movements of at least one person within the field of view 154. When the movements are detected, the personal safety system 100 is configured to send a text message, a movement notification, and/or other electronic alert to the smartphone 108 indicating to the user that movement has been detected near the vehicle 104. The movement notification is based on the detected movement and, in one embodiment, includes the time the movement occurred and an image of the detected movement. Upon receiving the alert, the user may stream live image data to the smartphone 108 to view the current surroundings of the vehicle 104, in order to assist in determining if it is safe to approach the vehicle 104.

In another embodiment, the personal safety system 100 processes the image data to identify objects near the vehicle 104 that could pose a safety threat to the user. For example, the personal safety system 100 detects that a package, box, a stationary person, or other element is near the vehicle 104. The personal safety system 100 sends an object notification to the smartphone 108 based on the detected object.

Additionally or alternatively, the personal safety system 100 is configured to notify users when crimes have occurred and/or have been reported in the area of the smartphone 108 and/or the vehicle 104. For example, the personal safety system 100 is configured to electronically connect to a database of reported crimes and/or safety events that are categorized by location. The personal safety system 100 compares the location data to the locations of the reported crimes and/or safety events to identify the crimes and/or safety events that are near (i.e. within one kilometer, five kilometers, or any other selected distance) the user. When a nearby crime and/or safety event that is near the user is located, then the personal safety system 100 causes a notification or other alert to be sent to the smartphone 108 and/or the vehicle 104 so that the user can decide how to best proceed having additional knowledge of the safety of the area.

The personal safety system 100, in some embodiments, is user configurable to automatically activate and to automatically deactivate based on the location data. When the personal safety system 100 is activated, the personal safety system 100 is configured to automatically trigger the emergency response, including according to the method 300 of FIG. 3. When the personal safety system 100 is deactivated, the personal safety system 100 does not automatically trigger the emergency response and does not apply the method 300 of FIG. 3. The personal safety system 100 can be manually activated and manually deactivated by the user using the smartphone 108 and/or the infotainment system of the vehicle 104, for example.

The automatic activation and deactivation of the personal safety system 100 prevents the personal safety system 100 from triggering the emergency response when the vehicle 104 and the user are in a safe location. Exemplary safe locations include a home garage, driveway, carport, or parking space of the user and/or of a trusted person. Accordingly, when the personal safety system 100 detects that the vehicle 104 is located in a safe location (as selected by the user), based on the location data, the personal safety system 100 is automatically deactivated. When the vehicle 104 leaves the safe location, as detected by processing the location data, the personal safety system 100 is automatically activated. For example, the personal safety system 100 is activated when the user walks to her vehicle in a parking garage at her workplace. When the user drives the vehicle 104 to her home and parks the vehicle 104 in a known location, such as her driveway, which has been previously identified to the personal safety system 100 as a safe location, then the personal safety system 100 detects that the vehicle 104 is in the safe location and the personal safety system 100 is deactivated. Accordingly, when the user walks by the vehicle 104 to check the mail or to perform other household duties, the deactivated personal safety system 100 does not start the approach timer, does not send the checkup data, does not start the response time period, and does not trigger the emergency response. In this way, the user can freely move around the vehicle 104 at home without having to respond to the checkup data. The personal safety system 100 is automatically activated when the vehicle 104 leaves the safe location and is parked in any location that is not a safe location as identified by the user.

The personal safety system 100 provides benefits to the user. For example, using the personal safety system 100, the user is made to feel safer when approaching the vehicle 104 alone and/or when the vehicle 104 is in an unsecure area. The personal safety system 100 also provides security to the user by alerting the user when there is someone or something near the vehicle 104. The personal safety system 100 enables the user to decide when it is safe to begin her approach to the vehicle 104 by providing the user (i.e. the smartphone 108) with reports of nearby crimes and/or other safety events. The personal safety system 100 is integrated with the vehicle 104 and is operable to trigger the emergency response completely automatically and without requiring the user to access the smartphone 108.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method of operating a personal safety system including a vehicle, comprising:
    automatically detecting that a smartphone is within a communication range using a wireless communication system of the vehicle;
    starting an approach time period with a controller of the vehicle or the smartphone when the smartphone is detected;
    sending checkup data from the vehicle to the smartphone using the wireless communication system when the smartphone fails to arrive at the vehicle prior to the approach time period elapsing; and
    triggering an emergency response by the vehicle and/or the smartphone when the vehicle fails to receive a response to the checkup data from the smartphone within a response time period.

2. The method as claimed in claim 1, further comprising:
    detecting that the smartphone has arrived at the vehicle by determining, with the controller of the vehicle, that the smartphone is located inside a cabin of the vehicle,
    wherein the emergency response is not triggered when the controller detects that the smartphone has arrived at the vehicle prior to the approach time period elapsing.

3. The method as claimed in claim 1, wherein automatically detecting that the smartphone is within the communication range comprises:
    broadcasting periodic messages from the wireless communication system; and
    detecting that the smartphone is within the communication range when the wireless communication system receives connection data sent from the smartphone, the connection data generated in response to the smartphone receiving one of the broadcasted periodic messages.

4. The method as claimed in claim 1, wherein:
    the wireless communication system includes a Bluetooth Low Energy ("BLE") system, and
    the BLE system is configured to send the checkup data from the vehicle to the smartphone when the smartphone is within the communication range.

5. The method as claimed in claim 1, wherein triggering the emergency response comprises:
    activating an alarm of the vehicle, activating an alarm of the smartphone, and/or automatically calling an emergency services department using the smartphone or a phone system of the vehicle.

6. The method as claimed in claim 1, wherein:
    the wireless communication system includes a phone system,
    triggering the emergency response comprises automatically calling and/or texting a predetermined emergency contact phone number using the smartphone or the phone system,
    the phone system is configured to send the checkup data to the smartphone, and
    the checkup data is a text message, phone call, and/or notification.

7. The method as claimed in claim 1, wherein the wireless communication system is a first wireless communication system and the method further comprises:
monitoring a position of the detected smartphone relative to the vehicle with a second wireless communication system of the vehicle;
detecting an unsafe condition or a safe condition based on the monitored position using the controller of the vehicle or the smartphone; and
starting the approach time period when the unsafe condition is detected.

8. The method as claimed in claim 7, wherein:
the first wireless communication system includes a Bluetooth Low Energy system, and
the second wireless communication system includes an ultra-wideband system having a plurality of anchor units fixedly connected to the vehicle.

9. The method as claimed in claim 1, further comprising:
detecting movement of at least one person within a field of view of at least one imaging device of the vehicle; and
sending a movement notification to the smartphone, the movement notification based on the detected movement.

10. The method as claimed in claim 1, further comprising:
receiving vital sign data with the smartphone, the vital sign data based on a heartrate, blood pressure, and/or speed of a person with the smartphone;
detecting an unsafe condition or a safe condition based on the vital sign data using the controller of the vehicle or the smartphone; and
starting the approach time period when the unsafe condition is detected.

11. The method as claimed in claim 10, wherein detecting the unsafe condition comprises:
comparing the heartrate to a predetermined heartrate range; and
detecting the unsafe condition when the heartrate is outside of the predetermined heartrate range.

12. The method as claimed in claim 10, further comprising:
generating the vital sign data with a wearable device operably connected to the smartphone.

13. A method of operating a personal safety system including a vehicle, comprising:
automatically detecting that a smartphone is within a communication range using a first wireless communication system of the vehicle;
monitoring a position of the detected smartphone relative to the vehicle with a second wireless communication system of the vehicle;
detecting an unsafe condition or a safe condition based on the monitored position using the controller of the vehicle or the smartphone;
starting an approach time period when the unsafe condition is detected;
sending checkup data from the vehicle to the smartphone using the first wireless communication system when the smartphone fails to arrive at the vehicle prior to the approach time period elapsing; and
triggering an emergency response by the vehicle and/or the smartphone when the vehicle fails to receive a response to the checkup data from the smartphone within a response time period,
wherein detecting the unsafe condition includes detecting that the position of the smartphone is substantially stationary relative to the vehicle, and
wherein detecting the safe condition includes detecting that the position of the smartphone is approaching the vehicle.

14. The method as claimed in claim 13, further comprising:
detecting that the smartphone has arrived at the vehicle by determining, with the controller of the vehicle, that the smartphone is located inside a cabin of the vehicle,
wherein the emergency response is not triggered when the controller detects that the smartphone has arrived at the vehicle prior to the approach time period elapsing.

15. The method as claimed in claim 13, wherein triggering the emergency response comprises:
activating an alarm of the vehicle, activating an alarm of the smartphone, and/or automatically calling an emergency services department using the smartphone or a phone system of the vehicle.

16. A personal safety system, comprising:
a wireless communication system of a vehicle configured to automatically detect that a smartphone is within a communication range of the wireless communication system; and
a controller operably connected to the wireless communication system, the controller configured to:
start an approach time period when the smartphone is detected by the wireless communication system;
send checkup data from the vehicle to the smartphone using the wireless communication system when the smartphone fails to arrive at the vehicle prior to the approach time period elapsing; and
trigger an emergency response by the vehicle and/or the smartphone when the vehicle fails to receive a response to the checkup data from the smartphone within a response time period.

17. The personal safety system as claimed in claim 16, further comprising:
a satellite location system operably connected to the controller and configured to generate location data; and
a phone system operably connected to the controller and configured to call and/or text to a predetermined phone number,
wherein the emergency response includes automatically activating the phone system to call and/or text the predetermined phone number and transmitting the location data to a device receiving the call.

18. The personal safety system as claimed in claim 16, further comprising:
an imaging device of the vehicle, the imaging device configured to generate image data,
wherein the controller is further configured to (i) process the image data to detect a movement of at least one person, and (ii) to send a movement notification to the smartphone from the vehicle, the movement notification based on the detected movement.

19. The personal safety system as claimed in claim 16, wherein the wireless communication system is a first wireless communication system and the personal safety system further comprises:
a second wireless communication system operably connected to the controller and configured to monitor a position of the detected smartphone relative to the vehicle,
wherein the controller is further configured to:
detect an unsafe condition or a safe condition based on the monitored position, and
start the approach time period when the unsafe condition is detected.

20. The personal safety system as claimed in claim 19, wherein:

the first wireless communication system includes a Bluetooth Low Energy system, and the second wireless communication system includes an ultra-wideband system having a plurality of anchor units fixedly connected to the vehicle.

* * * * *